United States Patent
Coury et al.

(10) Patent No.: US 6,645,510 B1
(45) Date of Patent: Nov. 11, 2003

(54) METHOD OF TREATING TOPICAL AILMENTS

(75) Inventors: William S. Coury, Sarasota, FL (US); Griscom Bettle, Sarasota, FL (US); Berno I. Pettersson, Perry, GA (US)

(73) Assignee: American Medical Research, Inc., Sarasota, FL (US)

(*) Notice: Subject to any disclaimer, the term of this patent is extended or adjusted under 35 U.S.C. 154(b) by 0 days.

(21) Appl. No.: 09/787,547

(22) PCT Filed: Jun. 30, 1999

(86) PCT No.: PCT/US99/14907

§ 371 (c)(1),
(2), (4) Date: Aug. 30, 2001

(87) PCT Pub. No.: WO00/00186

PCT Pub. Date: Jan. 6, 2000

Related U.S. Application Data (60) Provisional application No. 60/091,234, filed on Jun. 30, 1998.

(51) Int. Cl.[7] .............................. A61K 6/00; A61K 7/00
(52) U.S. Cl. ................ 424/401; 424/59; 424/78.06; 424/78.07; 424/78.02; 424/78.03; 424/484; 424/485
(58) Field of Search .............. 424/401, 53, 78.06, 424/78.07, 484, 485, 78.02, 78.03

(56) References Cited

U.S. PATENT DOCUMENTS

| | | | |
|---|---|---|---|
| 4,381,919 A | 5/1983 | Jacquet et al. | 8/405 |
| 4,567,203 A | 1/1986 | Bonadeo | 514/844 |
| 4,976,953 A | 12/1990 | Orr et al. | 424/47 |
| 5,561,116 A | * 10/1996 | Nakamura et al. | 514/23 |
| 5,804,167 A | 9/1998 | Schönrock et al. | 424/59 |
| 5,948,416 A | 9/1999 | Wagner et al. | 424/401 |

FOREIGN PATENT DOCUMENTS

| | | |
|---|---|---|
| CH | 680565 | 3/1990 |
| DE | 43 44 697 A | 6/1995 |
| EP | 0 058 853 | 9/1982 |
| EP | 0 336 901 | 10/1989 |
| JP | 53127838 | 8/1978 |
| JP | 63179812 | 7/1988 |
| SU | 1248604 A | 8/1986 |
| WO | WO 94/13257 | 6/1994 |
| WO | WO 96/32089 | 10/1996 |
| WO | WO 97/01326 | 1/1997 |
| WO | WO 98/29085 | 7/1998 |

* cited by examiner

Primary Examiner—Thurman K. Page
Assistant Examiner—Liliana Di Nola-Baron
(74) Attorney, Agent, or Firm—Needle & Rosenberg, P.C.

(57) ABSTRACT

A composition capable of forming a film that ionically bonds to the skin comprising one or more active agents, a nonionic or substantially nonionic first film forming component, one or more cationic surfactant and a liquid carrier.

26 Claims, 1 Drawing Sheet

FIG.1

METHOD OF TREATING TOPICAL AILMENTS

RELATED APPLICATIONS

This application claims priority to U.S. Provisional Patent Application No. 60/091,234, filed Jun. 30, 1998.

FIELD OF THE INVENTION

This invention relates generally to skin products, and particularly to emulsion-based skin products that can be applied to the skin to provide continuing antimicrobial, antiviral, antiseptic, and skin protecting or healing properties.

BACKGROUND OF THE INVENTION

People often use soaps and bactericides to remove and exterminate undesirable contaminants such as dirt and bacteria from the skin, especially the hands. These products are typically applied to the skin while washing the hands under running water. The products have a limited temporal effect, however, because they are washed from the skin along with the dirt and bacteria during the washing process. Conventional soaps and bactericides do not, therefore, provide any lasting effect after they have been used. However, in many occupations, such as the medical profession, it is important to minimize and destroy harmful bacteria and viruses immediately when they contact the skin. A skin product that provided continued protection against contaminants with which the skin comes into contact, after being applied to the skin, would therefore be highly desirable. Such skin products should be specifically formulated for the special demands of particular applications.

In some applications, the need for rapid and anti-bacterial and anti-viral activity is particularly important. For example, surgeons and medical care practitioners require surgical scrub products that sanitize their hands before surgery or like procedures. FDA requires these products to have increasing efficacy the longer they are used. That is, regulations require that surgical scrub products improve their performance versus basic soaps with repeated use.

Prior art surgical scrub products are harsh to the hands. A typical surgical scrub product contains over 60% ethyl alcohol. Those products are very effective at killing microorganisms, but are equally effective at removing skin oils that make the skin soft and substantially crack-free. When hands are cracked and sore, it is more difficult to perform delicate surgery.

A product that matched the rapid anti-microbial behavior of high-alcohol surgical scrubs, by use of formulations containing aggressive anti-microbial agents, but which simultaneously coated and protected the medical practitioner's hands would be especially valuable.

Nevertheless, some skin is so damaged that aggressive anti-microbial active ingredients are too irritating for use in skin-care products. People who have developed a latex intolerance are typical of this group, because allergic reactions to the proteins or other irritants in latex products make their hands red and sore to the point of bleeding. Such allergies can threaten the careers of health care practitioners. If a skin-care product could be formulated to form a layer that coated, soothed, and protected the skin, yet could serve as a protective base layer for additional layers containing anti-microbial active agents, health care practitioners could protect themselves from harmful latex proteins, yet protect their patients from pathogenic organisms.

A different special situation is presented for skin products formulated for children younger than six years old. This population has a well documented history of frequent infections, many of which are transmitted via the hands. Children often have fingers and such in their mouths, so special formulations are required to make a safe and effective skin protectant product for children. A product that could protect and simultaneously disinfect the hands of young children, but be safe for them to occasionally ingest would improve the health of this special population.

Another special situation is baby's bottoms. Babies are prone to diaper rash and the like. A product that was gentle to baby's skin, yet protected this tender skin from the bacteria of feces and urine would be of particular advantage.

A skin-care product could also be adapted to topically deliver active agents, such as drugs, continuously to wounded, burned or ulcerated skin, or skin otherwise lacking in normal integrity. For example, preparations for removing warts might purposefully deliver toxic or irritating agents to selected areas of wounded skin.

Yet another set of special situations is presented by skin-care products formulated to topically deliver medicinally active agents to burns and wounds. Optimum wound or burn care products should (1) reduce inflammation by delivering anti-inflammatory agents or biological precursors of anti-inflammatory agents, (2) provide necessary nutrients and building block precursors for the biologically produced prostaglandin, leucotriene, and thromboxane compounds which regulate inflammation and promote tissue healing or new skin growth at a burn site which may have impaired blood supply, (3) promote normal and/or healing microbial activity at the wound surface, yet inhibit outside infections caused by external pathogenic bacteria or viruses, and (4) optionally modify electrical charge density in and around the wound so as to attract biologically provided nutrients and building block precursors to the wound site, which may have a deficient blood supply.

It would be especially desirable to formulate products for the treatment of wounds, or thermal, chemical, or radiation bums, to accomplish the above-described functional objectives. It would be desirable to formulate a composition which promotes increased levels of biosynthesized prostaglandin hormones such as PGE1, PGE3, PGI2, which promote healing of damaged skin and tissue, and caused decreased levels of prostaglandin PGE2, which produces undesirable inflammatory responses at a wound site. It would also be desirable to provide building block precursors of the hormones and other necessary cellular components, such as vitamins, minerals, sulfur compounds, saturated and unsaturated fatty acids, neurotransmitters, anti-oxidants, and other compounds which promote healing.

Prior art products provide anti-inflammatory compounds, necessary nutrients, or antiseptic treatments followed by non-sterile conditions, but none of the prior art teaches combining all the above functions in one stable salve.

Of particular importance is the healing of wounds and decubitus ulcers. A decubitous ulcer often begins as a bed shearing force abrasion on an immobilized patient. Body pressure restricts blood flow where the skin is in contact with the mattress. Necrosis ensues within 30 minutes, and a Level 1 ulcer (bed sore) develops. In more severe cases, the epidermal layer is disrupted (for example by scratching) and bacteria enter the site. As the ulcer severity increases, a deep sore opens up in a conical fashion. In a Level 4 decubitous ulcer, the bone is often visible.

Prior art treatments of Level 4 decubitous ulcers first require sanitizing the wound to kill pathogenic microorganisms, as well as normally benign or beneficial micro flora. Medicines were subsequently applied to the sanitary wound, or heavy debridement of damaged tissue was repeatedly applied during prior art treatments. Healing is problematic using such treatments, typically taking 6 months, and is successful less than half the time.

Improved compositions and methods for successfully treating such ulcers within 1–2 months would substantially advance the art. Indeed, improved compositions and methods for treating thermal burns, radiation burns, surface wounds, deep wounds or ulcers, warts, or diaper rash would substantially advance the medical arts.

SUMMARY OF THE INVENTION

In accordance with the purpose(s) of this invention, as embodied and broadly described herein, this invention, in one aspect, relates to a method of treating or preventing ailments of the skin, comprising applying to the surface of animal skin or tissue an effective amount of a composition capable of forming a film that ionically bonds to the skin or tissue comprising the residue of: one or more active agents; a nonionic or substantially nonionic first film forming component; one or more cationic surfactants comprising one or more fatty moieties that are soluble in the first film forming component; and a liquid carrier.

In another aspect the invention provides a method of treating or preventing skin ailments comprising applying to the surface of animal skin or tissue an effective amount of a composition comprising the residue of: one or more quaternary ammonium compounds; one or more surfactants; one or more fatty esters; one or more fatty alcohols; and optionally one or more highly polar compounds; wherein the ratio of the sum of the moles of quaternary ammonium compounds, surfactants, and highly polar compounds to the sum of the moles of fatty esters and alcohols is from about 0.8 to about 1.2.

In still another aspect the invention provides a method of treating or preventing skin ailments comprising applying to the surface of animal skin or tissue an effective amount of an emulsion composition comprising the residue of a fatty phase, wherein: the fatty phase comprises fatty acids, glycerides, and optionally other fatty components, and the molar ratio of fatty acids to glycerides and other fatty components is from about 0.5 to about 5.5.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawing, which is incorporated in and constitute a part of this specification, illustrates several embodiments of the invention and together with the description, serve to explain the principles of the invention.

DESCRIPTION OF THE PREFERRED EMBODIMENTS

The present invention may be understood more readily by reference to the following detailed description of preferred embodiments of the invention and the Examples included therein.

Definitions and Use of Terms

Before the present compounds, compositions and methods are disclosed and described, it is to be understood that this invention is not limited to specific synthetic methods, or to specific formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a fatty ester" includes mixtures of fatty esters, reference to "a liquid carrier" includes mixtures of two or more such carriers, and the like.

It must also be noted that ingredients in the claimed compositions can be referred to by more than one term, because of the multiple functions that these ingredients perform. Thus, ascorbyl palmitate acts as both a film forming stabilizer an antioxidant, and vitamin; as do vitamin E and beta-carotene. Other examples include EPA, CLA, DHA, and GLA which act as prostaglandin stimulators, precursors to prostaglandins, and also stabilize the final film, and facilitate the migration of medicinals through this film, and thus to the skin; thereby enhancing the medicinal's topical absorption. All of the previously mentioned are considered fatty moieties of the final film. Another example is dimethyl benzethonium chloride which acts as an antimicrobial, and also enhances wound healing by modifying the charge at the wound site. Another example is the adduct of a nitrogenous organic base and a fatty acid, which can function both as an active agent and a constituent of a film forming component. A final example is arginine, and other amino acids which act as neurotransmitters which stimulate the healing process and also are nutrients for use at the wound site. Complexed minerals such as zinc sulphate and copper curcumin act as antimicrobials, antifungals and also provide nutrition to the wound for speedier healing.

Ranges are often expressed herein as from about one particular value, and/or to about another particular value. When such a range is expressed, it is to be understood that a more preferred range is typically from the one particular value and/or to the other particular value. Similarly, when values are expressed as approximations, by use of the antecedent "about", will be understood that the particular value is typically more preferred. It will further be understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a composition containing 2 parts by weight of component X and 5 parts by weight component Y, X and Y are present at a weight ratio of 2:5, and are present in such ratio regardless of whether additional components are contained in the composition.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a residue of NaCl in solution, under appropriate conditions, refers to the sodium anion and chloride cation in solution.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. The term "lower alkyl" intends an alkyl group of from one to six carbon atoms, preferably from one to four carbon atoms. The term "cycloalkyl" intends a cyclic alkyl group of from three to eight, preferably five or six carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms. "Surface" of skin or tissue means the exposed area of skin or tissue associated with a skin ailment, and thus can be below the level of surrounding skin or tissue for deep wounds, ulcers, and other ailments.

"Ailments of the skin" refers to skin disorders, and include, for example, skin lesions, wounds, ulcers, burns, radiation burns, diaper rash, blisters, acne, psoriasis, athlete's foot, and warts.

The term "debridement" as used herein refers to a procedure used in the treatment of burns, wounds, and ulcers, wherein the burn, wound, or ulcer is subjected to vigorous mechanical or pharmaceutical cleaning and/or sterilization, which can include treatment with strong anti-microbial agents, or cutting away scabs and dead or damaged tissue.

The term "burn" as used herein refers to tissue injury resulting from excessive exposure to thermal, chemical, electrical, or radioactive agents, or electromagnetic radiation.

"Optional" or "optionally" means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and alkyl where there is substitution.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

Discussion

The invention is a creme or lotion composition that is especially effective for treating or preventing skin related ailments. The composition, when applied to the skin, provides a protective film that promotes skin healing, and which can be modified to topically deliver medicinal ingredients.

The composition has several novel aspects. Thus, in one embodiment the invention provides a method of treating or preventing ailments of the skin, comprising applying to the surface of animal skin or tissue an effective amount of a composition capable of forming a film that ionically bonds to the skin or tissue comprising the residue of one or more active agents; a nonionic or substantially nonionic first film forming component; one or more cationic surfactants comprising one or more fatty moieties that are soluble in the first film forming component; and a liquid carrier.

In another aspect the invention provides a method of treating or preventing skin ailments comprising applying to the surface of animal skin or tissue an effective amount of a composition comprising the residue of: one or more quaternary ammonium compounds; one or more surfactants; one or more fatty esters; one or more fatty alcohols; and optionally one or more highly polar compounds; wherein the ratio of the sum of the moles of quaternary ammonium compounds, surfactants, and highly polar compounds to the sum of the moles of fatty esters and alcohols is from about 0.8 to about 1.2.

In still another aspect the invention provides a method of treating or preventing skin ailments comprising applying to the surface of animal skin or tissue an effective amount of an emulsion composition comprising the residue of a fatty phase, wherein: the fatty phase comprises fatty acids, glycerides, and optionally other fatty components, and the molar ratio of fatty acids to glycerides and other fatty components is from about 0.5 to about 5.5. In separate embodiments the molar ratio is from about 0.5 to about 3.5, and from greater than about 3.5 (i.e. above the range encompassed by "about 3.5) to about 5.5.

From about 20 to about 40 parts by weight of one or more active agents are typically present in the composition, although from about 25 to about 35 parts by weight are preferred. The ingredients that make up the first film forming component typically comprise from about 1 to about 5 parts by weight of the total composition, and preferably comprise from about 2 to about 4 parts by weight. The composition typically comprises from about 0.2 to about 5 parts by weight of cationic surfactant, and preferably comprises from about 1 to about 3 parts by weight cationic surfactant. From about 50 to about 80 parts by weight of the liquid carrier are typically present in the composition, although from about 60 to about 75 parts by weight are especially preferred.

The first film forming component is preferably insoluble in the liquid carrier, and present in the composition as an emulsion. When applied to the skin, the first film forming component forms a hydrophobic film that covers the skin as the liquid carrier evaporates. The hydrophobic film provides a suitable environment for skin or tissue to heal. By bonding to the skin, the film can also exclude water and harmful agents such as bacteria from the surface of the skin.

The hydrophobic film may also act as a foundation for imparting continuing properties to the skin. Antiviral and antibacterial agents can be incorporated into the film, and thereby provide residual protection against contaminants with which the skin may come into contact. The hydrophobic film may also act as a medium through which medicinal agents can migrate and be delivered to the skin.

The hydrophobicity of the film can, of course, vary. However, the film is preferably sufficiently hydrophobic, and the film forming component sufficiently insoluble, to exclude water (and dissolved active ingredients such as cleansers and bactericides) from the surface of the skin as a film is formed on the surface of the skin. The film that is formed is preferably sufficiently impervious to water to minimize the incidence of water (which can carry aggravating cleansers, bacteria and other undesirable constituents) migrating through the film barrier.

Numerous formulations can be used as the first film forming component. For example, the first film forming component can include natural and synthetic polymers and waxes. For reasons that will become apparent, preferred formulations solubilize fatty moieties, and can selectively incorporate fatty moieties from ionic compounds within their structure, while excluding other ionic moieties from the compound, upon drying to form a film. Waxes, which contain the esters of fatty acids and fatty alcohols (other than glycerol), are especially suitable ingredients for the first film forming component. Waxes that suitably interact with propolis to impart the desired properties to the film are especially preferred.

An especially suitable formulation for the first film forming component comprises natural or synthetic bees wax; propolis; one or more fatty acids; and one or more fatty alcohols. Fatty refers generally to high molecular weight aryl, aliphatic, cycloaliphatic, saturated or unsaturated, straight or branched aliphatic compounds, preferably saturated and/or aliphatic and/or straight The fatty acids and fatty alcohols typically comprise greater than 10 or 12 carbon atoms, and/or less than 32, 26, or 18 carbon atoms. Thus, in one embodiment the fatty acid comprises from about 10 to about 32 carbon atoms, and the fatty alcohol comprises from about 10 to about 32 carbon atoms. In a preferred embodiment the fatty acid comprises from about 12 to about 18 carbon atoms, and the fatty alcohol comprises from about 12 to about 16 carbon atoms. In an even more preferred embodiment, the fatty acid comprises stearic acid, and the fatty alcohol comprises cetyl alcohol or myristic alcohol. In addition to being an integral element of the film, the fatty acid also preferably acts as a surfactant after it has been neutralized. The fatty alcohol preferably acts as an emulsifying agent. The alcohol can be substituted with groups such as amides, alkyl, and allyl groups, to tailor the alcohol to a specific set of requirements.

The bees wax is preferably natural, with crude, filtered bees wax being especially preferred. The bees wax can, however, be synthetic, or substituted with other natural waxes, as long as the wax possesses a net positive charge and a chemical similarity to natural bees wax, and interacts favorably with propolis. A particularly suitable synthetic bees wax is the synthetic wax manufactured by Alzo, Inc. of Sayreville, N.J., under the trade name Waxenol-8-22 (arachidyl behenate).

The propolis may preferably comprise propolis wax or propolis resin. The propolis may constitute a distinct ingredient of the composition, or it may be added as part of another ingredient such as the bees wax. The weight ratio of propolis to bees wax preferably meets or exceeds the ratio at which propolis and bees wax naturally occur (about 26:74).

The first filming component may optionally further comprise the solution residue of a monoester monoglyceride. The acidic residue of the monoester monoglyceride preferably comprises from about 10 to about 18 carbon atoms, and most preferably comprises 12 carbon atoms. The monoglyceride may be unsaturated, and may have up to three double bonds. Saturated monoglycerides are, however, especially preferred. The monoglyceride may also be substituted with, for example, one or more alkyl groups, especially the lower alkyl groups. A particularly suitable monoglyceride is lauricidin (distilled glyceryl monolaurate).

The first film forming component typically comprises from about 1 to about 12 parts by weight monoester glyceride, from about 0.2 to about 3.0 parts by weight bees wax, from about 0.1 to about 1.5 parts by weight propolis, from about 1.5 to about 10 parts by weight of one or more fatty acids, and from about 1 to about 8 parts by weight one or more fatty alcohols, independently or in combination. The first film forming component preferably comprises from about 2 to about 6 parts by weight monoester glyceride, from about 0.5 to about 1.5 parts by weight bees wax, from about 0.2 to about 0.6 parts by weight propolis, from about 3 to about 5 parts by weight of one or more fatty acids, and from about 2 to about 4 parts by weight of one or more fatty alcohols, independently or in combination.

The composition also preferably comprises a cationic surfactant, preferably comprising one or more fatty moieties. It is believed that the cationic surfactant binds ionically to the anionic sites on the surface of the skin, and, because the fatty moieties from the cationic surfactant are solubilized in the first film, anchors the film to the skin. It is also believed that the surfactant, by drawing the film toward the skin, helps to exclude water from the surface of the skin. The surfactant is preferably sufficiently cationic to achieve this anchoring function. Similarly, the fatty moieties preferably are sufficiently soluble and large, and have sufficient interaction with the film, to achieve this anchoring function. For example, fatty moieties comprising from about 12 to about 22 carbon atoms, and especially fatty moieties comprising about 18 carbon atoms, are most preferred.

The cationic surfactant preferably makes up at least 0.10 wt. % of the composition, and preferably comprises no more than about 5.0 wt. % of the composition. Less cationic surfactant than 0.10 wt. % is not evenly distributed across the surface of the film, and therefore is not as effective to evenly bond the film to the skin, and uniformly exclude water from the surface of the skin. More cationic surfactant exceeds current FDA regulations.

In one embodiment the fatty cationic surfactant of the composition comprises an ammonium compound that is substituted with at least one lower alkyl moiety. In another embodiment the ammonium compound is substituted with from one to three lower alkyl moieties, and one or more fatty moieties comprising from about 8 to about 22 carbon atoms, preferably from about 16 to about 22 carbon atoms. The fatty moiety can preferably be aryl, aliphatic, cycloaliphatic, saturated or unsaturated, straight or branched. In a more particular embodiment the cationic surfactant comprises the solution residue of dimethyl distearyl ammonium chloride. A dimethyl, ditallow ammonium chloride residue, with its broader molecular weight distribution, is also preferred.

The liquid carrier for the composition can also vary. Indeed, any carrier that does not substantially interfere with the components or the function of the components, and which allows a film to form and thereby exclude the carrier from the skin surface as it evaporates, is suitable. Exemplary carriers include water, and lower molecular weight alcohols such as ethanol, isopropyl alcohol, sec-butyl alcohol, glycerin, and propylene glycol, although water is generally preferred for the particular ingredients described in this document.

The composition may comprise one or more active agents, which are chosen based upon the properties that one desires from the composition. For example, in one embodiment the composition may include an aggressive cleansing or skin preparation ingredient. Such active agents cleanse the surface of the skin immediately upon application of the composition to the skin, and cleanse the skin sufficiently before a film is formed from the first film forming component, and before the first film forming component excludes the active agents from the surface of the skin.

Cleansing ingredients may be capable of removing microbials, viruses, and other foreign contaminants from the surface of the skin. Cleansing ingredients may also be capable of scouring dead and dying layers of skin from the skin surface. The cleansing ingredient may suitably comprise non-ionic surfactants because:(1) this class of compounds readily cleanses the skin, and removes the fatty dead, and dying layers of the outer surface of the skin (the stratum disjunction and stratum corneum); (2) this class of compounds is typically very soluble in the water base of the composition; (3) this type of compound is an effective antiviral compound; and (4) this class of compounds allows the proper functioning of the other active ingredients of the composition.

Surfactants are particularly suitable because of their ability to cleanse at the interface of the liquid composition and the outer layers of the skin. A particularly suitable nonionic surfactant is sold under the trade mark Triton X-100, and comprises octoxylenol, most suitably having 9–10 repeating units of ethoxylation. Another particularly suitable nonionic surfactant is nonoxynol-9, which can be used alone or in combination with other surfactants.

Suitable antimicrobial and cleaning active agents that can be incorporated into the composition include propylene glycol, berberine sulfate, various quaternary ammonium compounds, such as dimethyl benzethonium chloride, benzalkonium chloride, benzoxonium chloride, and cetyl pyridinium chloride. Additional antimicrobial and cleansing agents include, but not limited to parachlorometaxylenol, nonoxynol-9, chlorohexadine gluconate, and lauricidin (glycerol monolaurate). Other active agents include skin healing emollient ingredients such as allantoin, aloe, dimethyl sulfone, dimethicone, fragrances and anti-oxidants.

It is also possible to include active agents with medicinal properties in the composition which, when delivered topically, are absorbed by the skin and metabolized. Any active agent that is fat soluble, or which can be rendered fat soluble, is a suitable candidate for delivery through the compositions of the present invention, because such agents are capable of migrating through the final film formed by the composition, and thereafter being topically delivered to the skin.

The medicinally active agents of the invention can be added singly, or in any combination. Each medicinally active agent typically comprises from about 0.01 weight % to about 3.0 weight percent of the composition, although active agents can be present, either singly or in combination, in quantities as high as 25 wt. %, 20 wt. %, 15 wt. %, 10 wt. %, or 5 wt. %. Most medicinally active agents are preferably present from about 0.01 weight % to about 1.0 weight percent. Preferred medicinally active agents include alkylglycerols, alkoxyglycerols, polyunsaturated fatty acids or polyunsaturated oils, fat soluble vitamins, sulfur compounds, minerals, antioxidants, amino acids, energy stimulators, steroidal hormones, or glycoprotein hormones. Preferred medicinally active agents also include a variety of other healing agents including glycyrrhizic acid, ribonucleic acids, aloe vera, allantoin, bioperine, berberine hydrochloride, colostrum, dexpanthenol, glucosamine salts, inositol, phytantriol, pyrolidine carboxylic acid, jojoba oil, symphytum officinal, polysorbate 80, vanilla extract, and adducts of a nitrogenous organic base and a fatty acid. Adducts of nitrogenous organic bases and fatty acids are especially appropriate for use in higher concentrations.

Glycerides, including mono-, di-, and triglycerides, and alkoxyglycerols and alkylglycerols, are particularly suitable as active agents, or as carriers for active agents, in topical applications. These components have independent medicinal properties, are capable of independently migrating through the film, and can also solubilize other fat soluble active agents and carry them through the first film to the surface of the skin. Particularly suitable glycerides typically comprise from about 10 to about 36 carbon atoms, can be conjugated or saturated, and are generally liquid at room temperature. Preferred glycerides include, lauricidin, vitamin D suspended in palm oil, conjugated linoleic acid ("CLA"), gamma linolenic acid ("GLA"), and eicosapentaenoic acid (EPA). Highly unsaturated oils are also especially suitable active agents in such topical applications because such oils have an antioxidant benefit when applied to the skin, and in addition they are effective transport vehicles for fat soluble active agents.

The polyunsaturated fatty acids used as medicinally active agents include conjugated linolenic acid, alpha-linolenic acid, alpha-linoleic acid, gamma linolenic acid, dihomo-gamma-linolenic acid, docosahexaenoic acid, eicosapentaenoic acid. The polyunsatured fatty oils useful in the invention include neem oil, shark liver oil, lemon oil, or squalene. Other fatty oils include lemon oil and squalane. Shark liver oil and/or neem oil are typically used at higher concentrations than other medicinally active agents, and are thus typically present at concentrations of up to 10, 5, or 3 wt. % of the composition.

Preferred fat soluble vitamins include vitamin A, vitamin D, vitamin E, vitamin K, a tocotrienol, lycopene, b-carotene, ascorbyl palmitate, and luteine. Preferred sulfur compounds include dimethylsulfone, zinc sulfate, or lipoic acid. Preferred minerals include zinc sulfate; zinc 1-monomethionine; and compounds of copper, calcium, magnesium, chromium, selenium, vanadium, cobalt, and silica. Compounds include salts and chelates, among others, and especially include calcium proprionate; copper porphyrin compounds, silicic acid or silica gel, and copper-curcumin.

Preferred anti-oxidants include ascorbyl palmitate, neem oil, squalene, ferulic acid, lipoic acid, grape seed extract, boswellin, and bilberry extract. Preferred amino acids include arginine, proline, glutamine, glycine, or trimethyl glycine, omithine alpha-ketoglutarate, and l-pyrroglutamic acid.

Energy stimulators are defined as compounds that provide easily metabolized sources of energy for the synthesis of ATP, and include bee pollen, natural honey, forskholin, and arginine. Preferred steroid hormones include cortisol, pregnenolone, and dehydroepiandrosterone When the composition is used to deliver medicinal active agents, the composition may preferably be modified by the addition of a suitable partitioning agent. Such partitioning agents preferably comprise from about 0.1 to about 3.0 wt. % of the composition, and even more preferably comprise from about 0.3 to about 1.5 wt. % of the composition. Partitioning agents can be incorporated in the composition in order to (1) facilitate the migration of active agents through the film, and (2) modulate the skin surface to facilitate penetration of the skin by the active agents. Suitable partitioning agents include carbomers, hydroxymethylcellulose, and glyceridyl monooleate, as taught, for example, by Ogiso et al., in J. Pharm. Sci. 84:482–488 (1995), by Roy et al., in Int'l Jnl of Pharm. 110:137–145 (1994), and by Niazy et al., in AAPS 9th Ann. Mtg. Abst. 7080. Pharm Res. 11:5194 (1994), the disclosure from the above references being hereby incorporated by reference.

A particularly effective class of partitioning agents for use with the compositions of the present invention are the nonionic polyethoxylated fatty ethers and alcohols. The molecular weight of these agents, and their limited solubility in the liquid carrier, cause them to form a layer on the surface of the skin even before the first film forming component forms a film. After the film has formed, it is believed that these agents interact with the cationic surfactants that are anchored to the film in a manner that facilitates the transmission of active agents from the film into the skin. Moreover, the ethoxylation of the compounds appears to minimize and prevent undue irritation of the skin by these surfactant compounds. The degree of ethoxylation also appears to affect the rate at which active agents are partitioned by the partitioning agent.

The effectiveness of the partitioning agent at facilitating the transmission of an active agent varies depending upon the size and polarity of the active agent. In general, the size of the active agent and the size of the partitioning agent are directly related, so that larger active agents require larger partitioning agents. The degree of ethoxylation of the partitioning agent is also directly related to the size of the active agent and the polarity of the active agent.

The degree of ethoxylation of the partitioning agent typically ranges from about 10 to about 400 units of ethoxylation, although it preferably ranges from about 10 to about 100 units of ethoxylation, and most preferably ranges from about 10 to about 20 units of ethoxylation. The size of the partitioning agent typically ranges from about 12 to about 36 carbon atoms, and preferably ranges from about 12 to about 18 carbon atoms. Particularly suitable partitioning agents include polyoxy(10) O-ethanol and ceto stearyl alcohol.

The composition may also comprise one or more anionic surfactants having one or more fatty moieties that are soluble in the first film forming component. The fatty acids that comprise the first film forming component are typically neutralized during preparation of the composition, and are especially suitable anionic surfactants. These surfactants are believed to be capable of forming a substantially discreet layer in the dried structure on the skin. Due to the unique structures of these anionic surfactants, they are capable of anchoring in the film through their fatty moieties, with their anionic portion being typically oriented on the opposite side of the film from the skin (because the anionic charge is repelled by the anionically charged skin surface). Because the anionic surfactant is located on the exposed side of the film, and is anchored in the film through its fatty moieties, the surfactant imparts continuing properties to the film. In a preferred embodiment the fatty moieties of the anionic surfactant comprise from about 12 to about 22 carbon atoms. A preferred anionic surfactant is a salt of stearic acid or sodium lauryl sulfate.

In another embodiment the composition comprises a nitrogenous organic base. The base stabilizes the emulsion when the composition comprises an emulsion, although how such stabilization is achieved is not well understood. The base is preferably triethanolamine, tromethamine, or a tris amino alcohol compound such as tris(hydroxymethyl) aminomethane, tris(hydroxymethyl)aminoethane, with triethanolamine and tromethamine being especially preferred. The nitrogenous base preferably forms an adduct with the fatty acid in the first film forming component. In a preferred embodiment the first film forming component is modified with a fatty acid/nitrogenous base adduct formed by mixing the fatty acid with one or more nitrogenous bases at temperatures between about 57 and about 80° C. Such adduct, in combination with the cationic surfactant, make at least one side of the first film essentially lipophilic and positively charged, and thereby attracted by the negatively charged skin.

Other ingredients may be included in the composition. Tetra sodium EDTA, for example, is preferably added to the composition in order to partially neutralize an emulsion of the composition. EDTA may also sequester any hard components of the water and further reduce the potential for any negative interactions between the hard components of the water and the active ingredients of the composition. From about 0 to about 0.5 parts by weight of EDTA are typically employed. A thickener can also be added to the composition in order to increase its viscosity, and obtain a creme product suitable for applying and rubbing into skin. Particularly suitable thickening agents include carboxypolymethylene (carbopol) and sodium carboxymethyl cellulose, present in the composition at from about 0 to about 0.6 parts by weight. Other ingredients that can be included in the composition include process aids such as glycerin and propylene glycol, emulsion stabilizers for the stearic acid such as cetyl alcohol, and preservatives such as chlorohexadine gluconate.

Additional ingredients can be added to the composition to build upon the layering effect of the composition, and to provide additional properties to the composition. In particular, in order to improve the residual properties of the composition, an outer film-forming component can be added to the composition. The outer film-forming component can be comprised of ingredients that form a substantially discreet film after the hydrophobic first film has formed, and therefore which surrounds the hydrophobic film. If properly formulated, the outer film traps and encapsulates active agents that may be contained in the composition.

Although other film-forming ingredients will be apparent to workers skilled in the art, a particularly suitable outer film forming ingredient is polyvinyl pyrrolidine (PVP), because it is initially soluble in water, but becomes insoluble upon drying and forming a film. It is believed that PVP, which can be added to the composition as a waxy non-soluble phase, coalesces and forms an outer film after the hydrophobic film has formed. It is believed that the outer film forms after the hydrophobic film has formed because the hydrophobic film forming ingredients respond more quickly to the evaporation of water from the composition and the resultant concentration of non-water ingredients in the composition. In essence, the hydrophobic film components are less soluble than the outer film ingredients and therefore precipitate first as water from the composition evaporates. Some of the active agents become entrapped between the hydrophobic film and the PVP outer film, it is further believed, because these active agents effectively precipitate from solution after the hydrophobic film has formed but before the outer film has coalesced. Because nonionic surfactants are the most soluble component of the composition, the outer film probably coalesces before the non-ionic surfactants precipitate from solution, and the outer film probably excludes and expels any non-ionic surfactants further from the skin, where they can provide desired residual effects.

It is believed that the composition of the invention forms one or more substantially discreet layers when applied to the skin. For example, the composition typically comprises a first hydrophobic film and a second outer film. Another layer can be present between these two layers that comprises active ingredients. For example, a layer of anionic moieties (from the fatty anionic surfactants) will typically coat the surface of the first hydrophobic film opposite the skin. Other active agents that precipitate from the composition before the second film forms can also form a layer between the first and outer films. Moreover, when the second film forms it can exclude other active agents that are still solubilized in the liquid carrier, and thereby form an additional layer on the outside of the outer film.

These layers will typically be substantially discreet. In many instances, however, various components of the composition will separate into different layers of the composition. This can happen, for example, if some of the ingredients that comprise the first film forming component are not incorporated in the film, or if some of the cationic surfactant doe not end up between the first film and the skin.

In some compositions the separation of ingredients among layers can be done by design. This is especially true of compositions used to deliver medicinal agents to the surface of the skin. In such compositions the medicinal agent will preferably be at least partially soluble in the first film. Some compositions may, however, comprise more medicinal agent in the composition than can be solubilized by the film, and as a result the medicinal agent may separate among the layers of the composition.

Thus, the first film that eventually forms from the first film forming component can incorporate in its structure various of the other ingredients contained in the composition. Active agents, in particular, are often incorporated into the film in order to enhance the effectiveness of the active agent.

The compositions of the invention preferably are about neutral, and even more preferably slightly basic, with pH typically not exceeding about 8.5, 8.0, 7.8, or 7.5, and typically not below about 7.1 or 7.5. For example, compositions having a pH of from about 6.5 to about 8.0 are preferred. Compositions having a pH of from about 7.1 to about 7.5 are even more preferred.

In another aspect the invention provides a phase stable emulsion comprising one or more quaternary ammonium compounds; one or more nonionic surfactants; one or more fatty esters; one or more fatty alcohols; and optionally one or more highly polar compounds. In a particularly preferred embodiment the above components are present at a preferred ratio at the moment that the emulsion is formed. Components that are added to the composition after the emulsion has formed are not included in the ratio. The ratio of the sum of the moles of quatemary ammonium compounds, surfactants, and highly polar compounds to the sum of the moles of fatty esters and alcohols is preferably from about 0.8 to about 1.2. In an even more preferred embodiment the ratio is about 1.0.

Highly polar compounds that are included in the ratio include those compounds that are ionic and that have a dipole moment that exceeds the dipole moment of methanol. Highly polar compounds are typically added to increase the solubility of nonpolar compounds in polar solvents, although they can also be added as active agents. For example, polar compounds that contain sulfur are preferred when using the composition to treat burns because they are a source of sulfur which is used to heal damaged skin. Highly polar compounds include, for example, dimethyl sulfone (MSM).

In another aspect the invention provides a composition that is present in the form of an emulsion comprising a fatty phase, wherein the fatty phase comprises the one or more fatty acids discussed above. The fatty phase further comprises one or more of the glycerides discussed above, typically mono-, di-, or tri-, but preferably triglycerides, alkoxyglycerols, and alkyl glycerols, such as are in natural shark liver oil. The fatty phase optionally comprises one or more of the other fatty components discussed above such as the fatty esters and fatty alcohols. In a preferred embodiment for delivering medicinal active agents to the surface of the skin, the molar ratio of the one or more fatty acids to the one or more glycerides and other fatty components is from about 1:2 to about 3.5:1, even more preferably from about 1:1 to about 2.5:1, and still even more preferably the ratio is about 2:1. It has been found that a composition having fatty acids and glycerides within this range of ratios are exceptional for topically delivering active agents, and that the ratio can be varied depending upon the topical effect desired for a particular system.

The invention also provides a process for preparing suitable compositions. In one aspect the invention provides a process for preparing a phase stable emulsion comprising: forming an aqueous phase; forming a second phase comprising one or more fatty acids, and one or more fatty alcohols and/or one or more fatty esters; mixing the first and second phases to form an emulsion; and mixing an organic base with the emulsion; wherein: (a) the emulsion optionally comprises one or more quaternary ammonium compounds, one or more surfactants, and/or highly polar compounds; and (b) the ratio of the sum of the moles of quaternary ammonium compounds, surfactants, and highly polar compounds, to the sum of the moles of fatty esters and fatty alcohols is from about 0.8 to about 1.2, preferably about 1.0. The various components are as defined above. The emulsion is preferably formed at a temperature of from about 57 C to about 80 C, preferably about 70 C. Moreover, the organic base is preferably mixed with the emulsion at a temperature of from about 57C, to about 80C, preferably about 70 C. The fatty ester(s) may optionally be added to the aqueous phase, although preferably they are included in the fatty phase.

The pH of the emulsion is preferably adjusted after the organic base is added to the emulsion to the pH levels discussed above, preferably from about 7.1 to about 7.8. Moreover, the emulsion can be stabilized with an emulsion stabilizer, such as a carbomer. One or more active agents may be added to the aqueous phase, the second fatty phase, or the emulsion, either before or after the emulsion is formed. In particular, the loading of certain active agents can be increased beyond a level at which an emulsion containing that active agent would normally be stable, by adding at least some of the active agent after the emulsion has been formed and preferably stabilized. This active agent loading procedure can be particularly important for providing the desired high concentrations of active agents such as lauricidin, chlorohexidine gluconate, dimethylsulfone, and other highly polar compounds. In a particularly preferred embodiment some or all of the active agents are cationic.

In another embodiment the invention provides a process for preparing a phase stable emulsion comprising: forming an aqueous phase; forming a second phase comprising one or more fatty acids, one or more fatty alcohols, and one or more fatty esters; mixing the first and second phases to form an emulsion at a temperature of from about 57 C to about 80 C; and mixing an organic base with the emulsion at a temperature of from about 57 C to about 80 C. In a particularly suitable embodiment the second phase comprises fatty acids at a molar ratio of fatty acids to glycerides and other fatty components of from about 1:2 to about 3.5:1, more preferably from about 1:1 to about 2.5:1, and most preferably about 2:1.

The compositions of this invention can also be characterized by the proportion of several components that are present in some of the most preferred formulations, including wax, propolis, fatty acids, fatty alcohols, glycerides, and quaternary ammonium compounds. Thus, in one embodiment, these components are present in the following weight percentages, based on the total weight of the composition:
1. Wax (which includes bees wax and other fatty esters): greater than about 0.05, or 0.1 wt. %, and/or less than about 5.0, 3.0, or 1.0 wt. %.

2. Propolis: zero, or greater than about 0.01, .025, .or .05 wt. %, and/or less than about 5.0, 3.0, or 1.0 wt. %.
3. Fatty acids: greater than about 0.5, 1.0, 2.0, or 3.0 wt. %, and/or less than about 15, 10, 8, and 6 wt. %.
4. Fatty Alcohols: greater than about 0.3, 0.5, 1.0, or 1.5 wt. %, and/or less than about 10, 8, or 6 wt. %.
5. Glycerides: greater than about 0.1, 0.5, or 0.9, and/or less than about 10, 8, and 6 wt. %.
6. Quaternary ammonium compounds: greater than about 0.1, 0.25, or 1.0, and/or less than about 12.0, 8.0, or 6.0 wt. %.

In one embodiment, these components are present in the following weight proportions:
1. Wax (which includes bees wax and other fatty esters): greater than about 0.1 or 0.4 parts, and less than about 2.0 or 1.0 parts.
2. Propolis: zero, or greater than about 0.025, and/or less than about 1.5 or 1.0 parts.
3. Fatty acids: greater than about 1.5 or 3.0 parts, and/or less than about 9 or 6 parts.
4. Fatty Alcohols: greater than about 0.3, 0.5, 1.0, or 1.5 wt. %, and/or less than about 10, 8, or 6 wt. %.
5. Glycerides: greater than about 0.1, 0.5, or 0.9, and/or less than about 10, 8, and 6 wt. %.
6. Quaternary ammonium compounds: greater than about 0.1 or 1.0, and less than about 8.0 or 6.0 parts.

The foregoing weight proportions apply to the composition before it is applied to the skin or tissue. Alternatively, because the applied lotion or creme (after the volatile components have evaporated) consists substantially of the foregoing components, the applied lotion or creme can be described by the foregoing proportions, based on the total of the foregoing ingredients equaling 100 wt. %.

Where possible, only highly purified ingredients should be used. For example, the fatty esters should be triple distilled when possible. Similarly, with the naturally occurring ingredients, unwanted compounds such as heavy metals may be removed if done so without destroying the desired properties of the natural molecules. Other compounds can, of course, be substituted for the specific ingredients disclosed herein, as discussed in the preceding paragraphs and as understood by workers skilled in the art.

Experimental

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts per 100 parts total weight of the final composition, which is equivalent to weight percent of the final composition, temperature is in ° C. or is at room temperature, and pressure is at or near atmospheric. Listed compounds are commercial grade.

EXAMPLE 1

An aqueous phase was first prepared by mixing the following components in the weight proportions listed. The aqueous phase was heated to 70 C and mixed until creamy and uniform.

| NAME OF INGREDIENT | WEIGHT % |
| --- | --- |
| D.I. water | 63.14 |
| Merquat 550 Polyquaternium-7 | 1.150 |
| Dimethyl Distearyl Ammonium Chloride | 1.300 |
| Berberine Hydrochloride | 0.013 |
| Active Agents | 4.75 |

A fatty phase was next prepared by mixing the following components in the weight proportions listed, and heating the mixture to 70 C. 0.500 weight % lemon oil were then added to the mixture. The fatty phase thus formed was then added to the aqueous phase, and mixed until uniformly consistent. Temperature was maintained at 70 C.

| NAME OF INGREDIENT | WEIGHT % |
| --- | --- |
| Stearic Acid | 3.750 |
| Cetyl Alcohol | 2.955 |
| Lauricidin | 3.150 |
| Propolis | 0.400 |
| Crude Bees Wax | 1.000 |
| Other Active Agents | 3.450 |

A third mixture was then prepared by combining the following ingredients at the weight proportions listed, at ambient temperature. The third mixture was then combined with the above mixture under high shear agitation to form an emulsion, with the temperature maintained at 70 C.

| NAME OF INGREDIENT | WEIGHT % |
| --- | --- |
| D.I. Water | 3.000 |
| TEA | 1.540 |
| Tetra Na EDTA (solid) | 0.300 |

The emulsion was allowed to cool to 50 C, and 4.53 weight %of processing aids were mixed with the emulsion. 2.5 weight % of other active agents were then added to the emulsion (including 0.25% chlorohexidine gluconate), and the pH was lowered to about 7.4 with citric acid.

EXAMPLE 2

An emulsion was formed substantially following the procedure of Example 1. The aqueous phase contained:

| NAME OF INGREDIENT | WEIGHT % |
| --- | --- |
| Water | 65.01 |
| Dimethyl Sulfone | 0.830 |
| Dimethyl Distearyl Ammonium Chloride | 4.500 |
| Active Agents | 3.683 |

The fatty phase contained:

| NAME OF INGREDIENT | WEIGHT % |
| --- | --- |
| Stearic Acid | 4.421 |
| Cetyl Alcohol | 4.119 |

-continued

| NAME OF INGREDIENT | WEIGHT % |
|---|---|
| Crude Bees Wax | 0.900 |
| Propolis | 0.750 |
| Lauricidin | 3.840 |
| Glycerides | 3.993 |
| Cetyl Lactate | 0.250 |
| Ascorbyl Palmitate | 0.150 |
| Active Agents | 0.575 |

4.66 weight % of processing aids were added to the mixture. 2.319 weight % of triethanolamine were then added to the mixture to adjust the pH to 6.9.

EXAMPLE 3

This example illustrates the preparation of an emulsion suitable for application to children's skin. An emulsion was formed substantially following the procedure of Example 1. The aqueous phase contained:

| NAME OF INGREDIENT | WEIGHT % |
|---|---|
| D.I. Water | 80.29 |
| Berberine hydrochloride | 0.05 |
| Dimethyl Distearyl Ammonium Chloride | 0.25 |
| Active Agents | 0.35 |

The fatty phase contained:

| NAME OF INGREDIENT | WEIGHT % |
|---|---|
| Stearic Acid | 3.0 |
| Cetyl Alcohol | 1.7 |
| Crude Bees Wax | 0.5 |
| Propolis | 0.1 |
| Lauricidin | 0.98 |
| Ascorbyl Palmitate | 0.2 |
| Active Agents | 0.15 |

The quantity of lauricidin added to the fatty phase was sufficient to balance the critical mole ratios for the formation and stability of the emulsion. 7.85 weight % of processing aids, (including a carbomer and propylene glycol) were added to the mixture. 1.35 weight % of triethanolamine were then added to the mixture to form the emulsion and adjust the pH to 7.1, to enhance the protection of tender young skin.

Additional lauricidin (3.15 weight %) was added after the emulsion was formed and stable, to provide the safe and non-toxic anti-microbial activity needed, but not disrupt the phase stability of the emulsion.

EXAMPLE 4

This example illustrates the preparation of an emulsion suitable for application to children's skin. An emulsion was formed substantially following the procedure of Example 1. The aqueous phase contained:

| NAME OF INGREDIENT | WEIGHT % |
|---|---|
| D.I. Water | 80.29 |
| Berberine hydrochloride | 0.02 |

-continued

| NAME OF INGREDIENT | WEIGHT % |
|---|---|
| Dimethyl Distearyl Ammonium Chloride | 0.1 |
| Active Agents | 0.35 |

The fatty phase contained:

| NAME OF INGREDIENT | WEIGHT % |
|---|---|
| Stearic Acid | 3.0 |
| Cetyl Alcohol | 1.7 |
| Crude Bees Wax | 0.4 |
| Propolis | 0.1 |
| Lauricidin | 0.895 |
| Glycerides | 0.65 |
| Ascorbyl Palmitate | 0.2 |
| Active Agents | 0.15 |

The quantity of lauricidin added to the fatty phase was sufficient to balance the critical mole ratios for the formation and stability of the emulsion. 6.60 weight % of processing aids (including a carbomer and propylene glycol) were added to the mixture. 1.25 weight % of triethanolamine and 0.1 weight % of tetra-sodium EDTA were then added to the mixture to form the emulsion and adjust the pH to 6.8, to enhance the protection of tender young skin.

Additional lauricidin (3.485 weight %) was added after the emulsion is formed and stable, to provide the safe and non-toxic anti-microbial activity needed, but not disrupt the phase stability of the emulsion.

EXAMPLE 5

An emulsion was formed according to Example 1, except that chlorohexidine gluconate (CHG) was added at 0.69 weight % (on an active basis, using a 20% aqueous solution of CHG). The subsequent emulsion was low in viscosity, and caused a perception of an unpleasant rush of blood to the hands. Users feared their hands would be hurt with continued use.

Accordingly, in an improved procedure, the Example 1 emulsion was prepared (except for a lowering of water, to compensate for water to be added later with the CHG) but the 0.69 weight % of CHG was added after the emulsion was stable and cooled to 50° C. The emulsion prepared by the improved procedure had good viscosity, and eliminated the perception of blood rush to the hands.

EXAMPLE 6

This example illustrates the preparation of a neutral emulsion having only a small quantity of active agents and non-ionic surfactants, suitable for application to damaged, irritated or bleeding skin. Such emulsions are typically applied as a base coat on damaged skin prior to applying an emulsion having potentially irritating agents, such as the CHG in the emulsion of Example 1. An emulsion was formed substantially following the procedure of Example 1. The aqueous phase contained:

| NAME OF INGREDIENT | WEIGHT % |
|---|---|
| D.I. Water | 64.47 |
| Dimethyl Distearyl Ammonium Chloride | 4.50 |
| Dimethylsulfone | 0.636 |
| Active Agents | 0.60 |

The fatty phase contained:

| NAME OF INGREDIENT | WEIGHT % |
|---|---|
| Stearic Acid | 3.91 |
| Cetyl Alcohol | 3.50 |
| Lauricidin | 4.00 |
| Glycerides | 3.422 |
| Active Agents | 0.15 |

11.36 weight % of processing aids were added to the mixture (including a carbomer stabilizer and propylene glycol). 3.1 weight % of triethanolamine and 0.1 weight % of tetra-sodium EDTA was then added to the mixture to form the emulsion and adjust the pH to 7.1

EXAMPLE 7

This example illustrates the preparation of a composition for removing warts. An emulsion was formed substantially following the procedure of Example 1. The aqueous phase contained:

| NAME OF INGREDIENT | WEIGHT % |
|---|---|
| D.I. Water | 55.23 |
| Dimethyl Distearyl Ammonium Chloride | 2.50 |
| Dimethylsulfone | 1.0 |
| Merquat 550 | 1.15 |
| Berberine Hydrochloride | 0.30 |
| Zinc Sulfate | 0.20 |
| Arabino Galactan | 0.25 |
| Triton X-100 | 1.0 |
| Nonoxynol-9 | 1.0 |
| Pyrolidine Carboxylic Acid | 0.2 |
| Poly oxy 10 | 2.0 |
| Aloe Vera | 0.25 |

The fatty phase contained:

| NAME OF INGREDIENT | WEIGHT % |
|---|---|
| Stearic Acid | 4.1 |
| Cetyl Alcohol | 3.82 |
| Lauricidin | 3.80 |
| Crude Bees Wax | 0.4 |
| Propolis | 0.2 |
| Allantoin | 0.3 |
| Lemon Oil | 0.8 |
| Vitamin E Acetate | 0.4 |
| Ascorbyl Palmitate | 0.2 |
| Glycetyl decanoate | 0.5 |
| Neem Oil | 0.758 |
| Shark Liver Oil | 2.50 |
| Eicosapentaenoic Acid | 0.36 |
| Conjugated Linoleic Acid | 0.36 |
| Gamma Linolenic Acid | 0.36 |
| Tetra Na EDTA | 0.3 |

-continued

| NAME OF INGREDIENT | WEIGHT % |
|---|---|
| Triethanolamine | 1.724 |
| Carbomer 940 NF | 0.12 |
| Propylene Glycol | 3.5 |

A third mixture of 3 weight % water, 1.724 weight % triethanolamine, and 0.3 weight % tetra-sodium ethylene diamine tetraacetic acid was formed, then mixed with the aqueous and fatty phases at 70° C. to form the emulsion. The emulsion was cooled to 55° C., and mixture of 3.5 weight % water, 0.12 weight % Carbomer 940 NF, 3.5 weight % propylene glycol, and 0.755 weight % of the dimethylsulfone, were added to the emulsion. The emulsion was cooled to 50° C., and 0.1 weight % of Boswellin, 0.3 weight % of NDHA, 0.3 weight % of Tomatine, 0.01 weight % Vitamin A, 0.1 weight % of Vitamin D, and 0.2 weight % of Lycopene were mixed with the emulsion.

EXAMPLE 8

This example illustrates the preparation of a composition for treating burns. An emulsion was formed substantially following the procedure of Example 1. The aqueous phase contained:

| NAME OF INGREDIENT | WEIGHT % |
|---|---|
| D.I. Water | 59.825 |
| Dimethyl Distearyl Ammonium Chloride | 4.7 |
| Dimethylsulfone | 0.83 |
| Merquat 550 | 1.15 |
| Triton-X-100 | 0.0 |
| Tomatine | 0.30 |
| Boswellin | 0.10 |
| Arabino Galactan | 0.25 |
| Active Agents | 2.79 |

The fatty phase contained:

| NAME OF INGREDIENT | WEIGHT % |
|---|---|
| Stearic Acid | 4.1 |
| Cetyl Alcohol | 3.82 |
| Lauricidin | 4.00 |
| Crude Bees Wax | 0.9 |
| Propolis | 0.3 |
| Other Active Agents | 5.203 |

A third mixture of 3 weight % water, 1.577 weight % triethanolamine, and 0.4 weight % tetra-sodium ethylene diamine tetraacetic acid was formed, then mixed with the aqueous and fatty phases to form the emulsion. A mixture of 3.0 weight % de-ionized water, 4.42 weight % process aids (including a carbomer stabilizer), 0.21 weight % dimethylsulfone, and 0.275 weight % of Active ingredients were then mixed with the emulsion.

EXAMPLE 9

This example illustrates the preparation of another composition for treating burns. An emulsion was formed substantially following the procedure of Example 1. The aqueous phase contained:

| NAME OF INGREDIENT | WEIGHT % |
|---|---|
| D.I. Water | 50.068 |
| Dimethyl Distearyl Ammonium Chloride | 4.7 |
| Dimethylsulfone | 0.597 |
| Active Agents | 3.44 |

The fatty phase contained:

| NAME OF INGREDIENT | WEIGHT % |
|---|---|
| Stearic Acid | 4.1 |
| Cetyl Alcohol | 3.82 |
| Lauricidin | 3 |
| Squalene | 0.6 |
| Ascorbyl Palmitate | 0.26 |
| Other Surfactants | 0.6 |
| Other Active Agents | 5.385 |

The aqueous and fatty phases were mixed, then a third mixture of 3 weight % water, 1.577 weight % triethanolamine, and 0.4 weight % tetra-sodium ethylene diamine tetraacetic acid was added to the aqueous and fatty phases at 70° C. to form the emulsion. The emulsion was cooled to 55° C., and 3.0 weight % de-ionized water, 8.92 weight % process aids (including a carbomer and propylene glycol), 0.403 weight % dimethylsulfone, and 5.86 weight % of Active ingredients was mixed with the emulsion. The emulsion was then cooled to 50° C., and then another 0.4 weight % of active ingredients were added to the stabilized emulsion.

EXAMPLES 10–14

These examples illustrate compositions for treating burns and skin lesions. The emulsions were formed substantially following the procedures described above. The final compositions contained:

| Example # | 10 | 11 | 12 | 13 | 14 |
|---|---|---|---|---|---|
| Application of Composition | Deep Wounds | Surface Wounds | Thermal Burns | Radiation Burns | Deep Wounds |
| Name of Ingredient | Wt % | Wt % | Wt % | Wt % | Wt % |
| Water | 60.364 | 70.06 | 67.67 | 70.796 | 63.25 |
| Dimethyl Distearyl Ammonium Chloride | 4.5 | 4.5 | 4.5 | 4.5 | 4.5 |
| Aloe Vera | 0.250 | 0.100 | 0.250 | 0.400 | 0.300 |
| Allantoin | 0.600 | 0.150 | 0.500 | 0.300 | 0.300 |
| Ferulic Acid | 0.080 | 0.050 | 0.080 | | 0.100 |
| Dimethylsulfone (Pre-emulsion) | 0.817 | 0.700 | 0.761 | 0.830 | 0.647 |
| Pyrolidine Carboxylic Acid | 0.200 | 0.200 | 0.100 | 0.200 | 0.200 |
| Dimethyl Benzethonium Chloride | 0.250 | 0.500 | 0.250 | 0.250 | 0.250 |
| Colostrum | 0.200 | 0.200 | 0.200 | 0.300 | 0.300 |
| Lipoic Acid | 0.050 | 0.050 | 0.080 | 0.080 | 0.080 |
| Bilberry | 0.200 | | | | |
| Grape Seed Extract | 0.100 | 0.200 | 0.200 | 0.400 | 0.300 |
| Zinc Methionone | 0.200 | | 0.100 | 0.200 | 0.200 |
| Zinc Sulfate | 0.100 | 0.200 | 0.100 | 0.200 | 0.200 |
| Silica Gel | 0.100 | 0.100 | 0.050 | 0.100 | 0.100 |
| Bioperine | 0.080 | 0.080 | 0.080 | 0.080 | 0.080 |
| Arginine | 0.300 | 0.250 | 0.250 | 0.300 | 0.300 |
| Proline | 0.100 | 0.100 | 0.100 | 0.100 | 0.100 |
| L-Glutamine | 0.100 | | 0.100 | 0.100 | 0.400 |
| Trimethyl Glycine | | | 0.100 | | |
| Glycine | | | 0.100 | | |
| Cu-Curcumin | 0.100 | | | 0.100 | 0.050 |
| Glycyrrhizic Acid | | | | 0.050 | 0.050 |
| Glucosamine HCl | | | | 0.100 | 0.100 |
| Natural Honey | | | | | 0.200 |
| RNA | | | | 0.100 | 0.100 |
| Inositol | 0.200 | | | | |
| Boswellin | | 0.150 | | | |
| Berberine HCl | | 0.050 | | | |
| Dexpanthenol | 0.330 | 0.330 | 0.630 | 0.330 | 0.330 |
| Phytantriol | 0.110 | 0.110 | 0.315 | 0.110 | 0.110 |
| Tetra Sodium EDTA | 1.250 | 0.750 | 1.250 | | |
| Polysorbate-80 | .200 | 0.100 | 0.300 | 0.040 | |
| Symphytum | | | 0.025 | | |
| Stearic Acid | 4.100 | 4.128 | 4.100 | 4.100 | 4.100 |
| Cetyl Alcohol | 3.820 | 3.820 | 3.820 | 3.820 | 3.820 |
| Crude Beeswax | 0.900 | 0.900 | 0.900 | 0.600 | 0.600 |
| Lauricidin | 3.800 | 3.700 | 4.000 | 4.000 | 3.800 |
| B-Carotene - 95% | | | | 0.016 | |
| Ascorbyl Palmitate | 0.200 | 0.150 | 0.150 | 0.200 | 0.200 |
| Neem Oil | 0.300 | 0.300 | 0.400 | 0.495 | 0.514 |
| Shark Oil | 2.310 | 2.000 | 1.592 | 3.300 | 2.000 |
| Conjugated Linoleic Acid | 0.400 | 0.400 | 0.484 | 0.315 | 0.400 |
| Eicosapentaenoic Acid | 0.500 | 0.500 | 0.484 | 0.315 | 0.500 |
| Lemon Oil | 0.200 | 0.400 | 0.200 | 0.200 | 0.200 |
| Pregnenolone | 0.200 | 0.200 | 0.200 | | |
| Dihomo Gamma Linolenic Acid | 0.100 | 0.100 | 0.100 | 0.100 | 0.100 |
| Cetyl Lactate | 0.250 | 0.250 | | | |
| Gamma Linolenic Acid | 0.400 | 0.400 | 0.484 | 0.315 | 0.400 |
| B-Carotene - 95% | 0.016 | 0.002 | 0.0160 | 0.188 | 0.002 |
| Propolis | 0.200 | 0.300 | 0.300 | 0.025 | 0.025 |
| Water | 0.000 | 0.00 | | | |
| Triethanolamine | 12.400 | 5.163 | 5.500 | 5.400 | |
| Propylene Glycol | 4.000 | 3.500 | 4.000 | 4.000 | 4.000 |
| Water | 0.000 | 0.00 | | | 2.000 |
| Carbomer 980 NF | 0.500 | 0.500 | 0.500 | 0.500 | |
| Carbomer 940 NF | | | | | 0.080 |
| Glycerin | 0.300 | 0.300 | 0.300 | 0.300 | 0.300 |
| Vitamin A | 0.002 | 0.002 | 0.002 | 0.002 | 0.002 |
| Vitamin D | 0.002 | 0.002 | 0.002 | 0.002 | 0.002 |
| Vitamin K | 0.002 | 0.002 | 0.002 | 0.002 | 0.002 |
| Vitamin E | 0.150 | 0.150 | 0.150 | 0.250 | 0.250 |
| B-Carotene - 95% | 0.188 | 0.011 | | | |
| Vanilla Extract | 0.050 | 0.060 | 0.050 | 0.050 | 0.050 |
| Tocotrienol | 0.080 | 0.080 | 0.080 | 0.080 | 0.080 |
| Pregnenolone | | | | 0.200 | 0.200 |
| Lycopene | 0.100 | | 0.100 | 0.300 | 0.100 |
| Dimethylsulfone (Post Emulsion) | | | 0.239 | | |
| Tetra Na EDTA | | | | 0.400 | 0.400 |
| Water | | | | | 1.750 |
| Triethanolamine | | | | | 1.577 |
| to give pH 6.9 ± .1 | | | | | |

EXAMPLE 15

Figure 1:
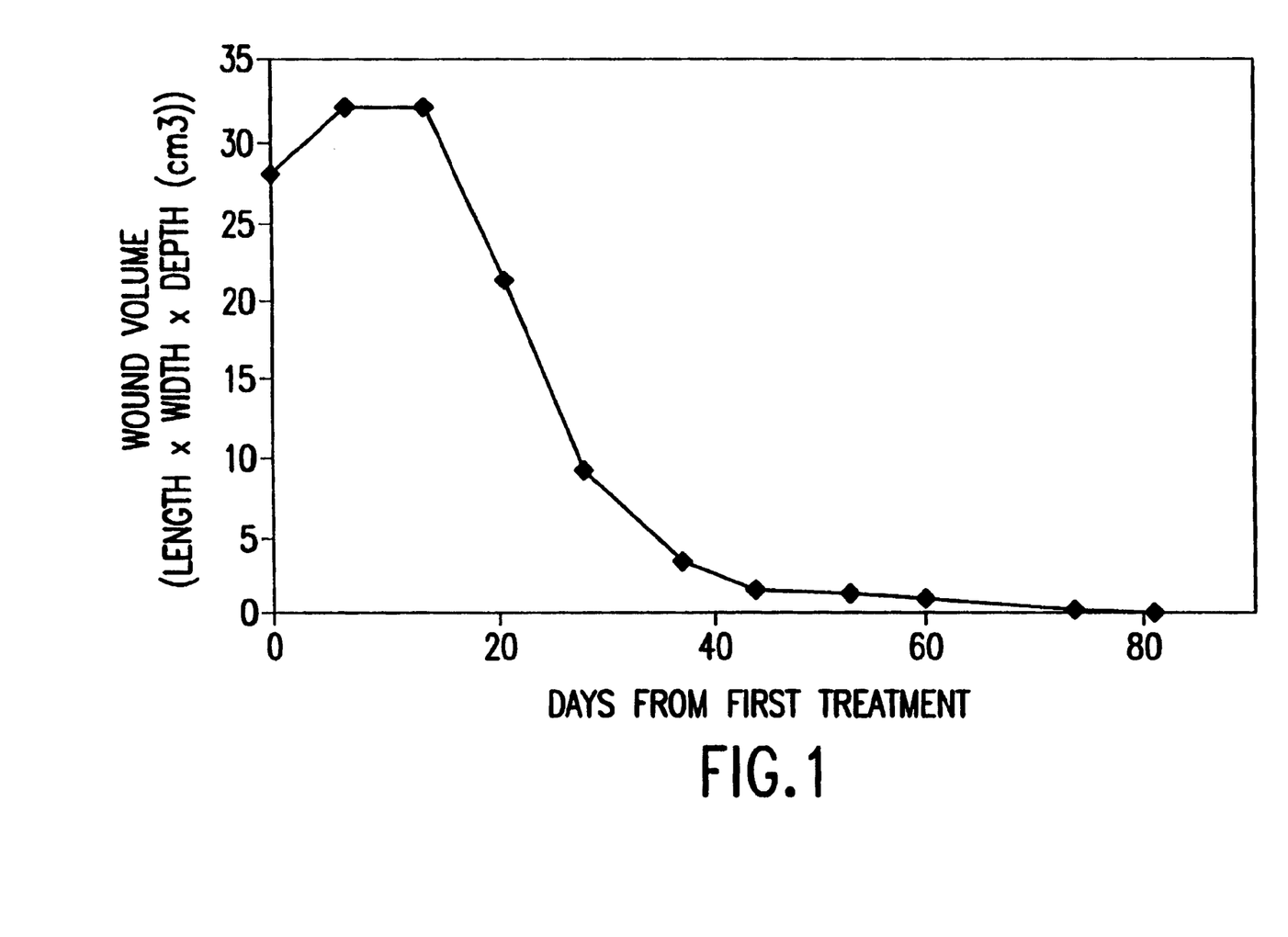
FIG. 1 shows estimated volume of a patient's heel wound versus time in days, wherein the wound was undergoing treatment with the methods and compositions of the inventions, as disclosed in Example 15.

A product having the composition of Example 10 was used to treat a wound on a patient's heel that had resisted healing for over six weeks. Two to three times per day the open wound was packed with the product and covered with gauze. The length, width, and depth of the wound were measured approximately weekly, and the estimated volume of the wound was calculated and plotted versus time, as shown in FIG. 1.

EXAMPLE 16

A nurse dropped a hot curling iron between her breasts while dressing, causing a severe burn. The nurse subsequently applied a product having the composition of Example 12 to the burn. Not only did the burn heal completely, but no scar tissue was formed in this sensitive area.

EXAMPLE 17

Radiation burns are often a byproduct of radiation treatment of cancer. A product having the composition of Example 13 was applied topically to the skin of predetermined site of radiation treatment for a cancer patient before the radiation treatment. No burn was apparent after radiation therapy, and the attending physician described the non-event as "extraordinary".

EXAMPLE 18

The following protocol is used to prevent radiation-induced dermatitis and related skin injury using, for example, the composition of Example 13. Following the procedures for application carefully will ensure successful completion of radiation therapy without injury to the overlying skin and tissue:
1. Apply composition to areas marked for radiation therapy. Apply one (1) hour before radiation therapy.
2. Reapply immediately after radiation therapy.
3. Technique for application:
   a. With a clean cotton swab or a tongue blade, apply thin layer or coating to cover completely the marked areas for radiation therapy;
   b. Wait fifteen (15) seconds;
   c. Then, with a clean fingertip, rub into skin until fully absorbed.

EXAMPLE 19

The following protocol is used to maintain the skin in a healthy state during and after radiation therapy and will help prevent skin infections and other tissue damage from developing using, for example, the composition of Example 13.
1. Apply twice daily, on day of therapy—two (2) or four (4) hours after last application of composition of Example 13, and at bedtime.
2. On off days (no radiation therapy), apply three (3) times (morning, noon and night).
3. Technique for application is the same as described above for Example 18.
4. Wait fifteen (15) seconds, then rub into skin.

EXAMPLE 20

The following protocol is used to treat first, second, and third degree burns, using, for example, the compositions of Examples 10 & 11. Carefully following the procedures, full application will ensure successful healing with limited scarring at the burn site. Should any signs of localized or systemic infection occur, then aggressive antibiotic therapy is indicated and should be started immediately.

Initial Assessment of Burns

Emergent phase (0 to 72 hours post-burn). Clinical assessment and complete history and physical are critical during this phase of treatment.
1. Rule of nines is the easiest way to assess the extent of burn in adults.
2. Depth of burns.
   a. Partial thickness (intradermal)—these injuries may appear red or pink, often with blister formation;
   b. Full thickness—these injuries may be charred or marble-gray in color, dry and anesthetic;
   c. Partial thickness burns may also have some anesthesia at times due to nerve endings being injured so the pain response is useful only when positive indicating a partial thickness burn.

Directions for Use

1. Apply to entire area of burn with some overlap onto normal tissue to ensure that all unrecognized burned tissue is covered (early in the course of a burn, the area of burn may be underestimated).
2. Apply immediately or as soon as possible to the burned areas after estimates of percent of burn and degree of burn are completed.
3. Apply two (2) to three (3) times per day.
4. Cover the treated burn with one (1) layer of flexible gauze-like conform, etc.
5. Debridement is not necessary, and in some embodiments may be avoided during one or more applications, but will generally occur with the dressing change. More extensive debridement of blisters or eschar should be done as is clinically indicated.
6. Continue applications until patient is healed.

EXAMPLE 21

The following protocol is useful for treating stage 1, stage 2, stage 3, or stage 4 wounds, using the composition set forth in Example 11 (for stage 1 and stage 2 wounds) and Examples 10 and 14 (for stage 3 and stage 4 wounds). The antibiotic concentration for stage 1 and stage 2 wounds is greater typically to allow penetration through the epidermis and dermis and superficial wounds.

Classifications

Stage 1: Red, unbroken skin, no blanching.
Stage 2: Blistered or broken skin. Wound base moist and pink. Free of necrotic tissue.
Stage 3: Extends through the dermis to involve subcutaneous tissue.
Stage 4: Deep tissue destruction extending through subcutaneous tissue, may involve muscle layers, joint and/or bone. Present as a deep crater. May include necrotic tissue.
Note: Any wound with eschar cannot be properly staged and should be classified as a full thickness wound.

Directions for Use

1. Make all appropriate measurements of size, and dimensions of erythema and eschar.
2. Culture wound.
3. Debride wound if necessary.
4. Make accurate assessment of depth using a sterile swab and measuring the depth from the swab.
5. For stage 1 and stage 2 wounds, apply a thin coat of the composition to the wound and let stand for 30 seconds. Then, topically run the formula into the skin observing the oxidation effect.
6. For stage 3 and greater wounds, apply the composition making sure to completely fill the wound, including any voids, channels, or cavities in the tissue or walls of the wound, to slightly above epidermal level.
7. Cover the wound with one (1) layer of gauze bandage and wrap with conform to keep the areas of tunneling or undermining fully saturated and dressings intact.
8. Change dressings two (2) or three (3) times daily, repeating this process.

Notes

1. It is not necessary to use any microbial cleaners during the healing process. Irrigating with normal saline may be appropriate.
2. If there appears to be evidence of topical wound infection that stays localized and does not extend greater than 0.5 to 1.0 centimeters beyond the wound margin and the patient does not become febrile, then proceed with the application as prescribed. The topical infection characteristically remits within 12–36 hours. If the patent becomes febrile or if there is a question of cellulitis, then proceed with vigorous systemic antibiotic therapy in addition to the treatment.
3. If significant eschar formation is present, debridement is indicated prior to initial treatment. Characteristically, the appropriate treatment will soften the eschar formation and gently lift this to extrusion as part of the healing process in three (3) to six (6) days if sharp and blunt disection is not readily available.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating skin or tissue, comprising applying to the surface of animal skin or tissue an effective amount of a composition capable of forming a film that ionically bonds to the skin or tissue comprising the residue of:
   a. one or more active agents;
   b. a nonionic or substantially nonionic first film forming component comprising one or more fatty esters, one or more fatty acids, and one or more fatty alcohols;
   c. one or more cationic surfactants comprising one or more fatty moieties that are soluble in the first film forming component;
   d. an adduct obtained by mixing a nitrogenous organic base with the fatty acid in the first film forming component, and
   e. a liquid carrier.
2. The method of claim 1 wherein the first film forming component comprises the residue of:
   a. one or more waxes;
   b. propolis;
   c. a fatty acid comprising from about 10 to about 26 carbon atoms; and
   d. a fatty alcohol comprising from about 10 to about 26 carbon atoms.
3. The method of claim 2 wherein the one or more waxes comprise natural or synthetic bees wax.
4. The method of claim 2 wherein the first film forming component further comprises a monoester monoglyceride.
5. The method of claim 1 wherein the cationic surfactant comprises an ammonium compound that is substituted with one or more lower alkyl moieties, and one or more fatty moieties comprising from 16 to 22 carbon atoms.
6. The method of claim 1 wherein the cationic surfactant comprises the solution or reaction residue of dimethyl distearyl ammonium chloride.
7. The method of claim 1 wherein the composition further comprises a partitioning agent.
8. The method of claim 7 wherein the partitioning agent is a nonionic polyethoxylated fatty ether or alcohol.
9. The method of claim 1 wherein the composition further comprises from about 0.1 to about 3.0 wt. % polyethyloxylated ether or alcohol.
10. The method of claim 1, wherein the nitrogenous organic base is triethanolamine.
11. The method of claim 1 wherein the fatty acid is stearic acid, conjugated linolenic acid, alpha linolenic acid, gamma linolenic acid, dihomogamma linolenic acid, docosahexaenoic acid, or eicosapentaenoic acid.
12. The method of claim 1, wherein the composition comprises a phase stable emulsion comprising the residue of:
   a. one or more quaternary ammonium compounds;
   b. one or more surfactants;
   c. one or more fatty esters;
   d. one or more fatty alcohols; and
   e. optionally one or more highly polar compounds;
   wherein the ratio of the sum of the moles of quaternary ammonium compounds, surfactants, and highly polar compounds to the sum of the moles of fatty esters and alcohols is from about 0.8 to about 1.2.
13. The method of claim 1, wherein the composition is in the form of an emulsion for delivering one or more medicinal active agents to the surface of the skin, comprising a fatty phase, wherein the fatty phase comprises one or more fatty acids and wherein the one or more active agents comprise one or more medicinally active agents.
14. The method of claim 13 wherein the fatty phase further comprises one or more glycerides, and optionally comprises other fatty components, wherein the molar ratio of the one or more fatty acids to the one or more glycerides and other fatty components is from about 0.5 to about 5.5.
15. The method of claim 14 wherein the ratio is about 2.0.
16. The method of claim 3 wherein the first film component is modified with a stearic acid/nitrogenous base adduct.
17. The method of claim 1 wherein the composition has a pH of from about 6.5 to about 8.5.
18. The method of claim 1 wherein the composition has a pH of from about 7.1 to about 7.8.
19. The method of claim 1, wherein the active agent comprises from about 0.01 weight % to about 5.0 weight percent of:
   a. an alkylglycerol;
   b. an alkoxyglycerol;
   c. a polyunsaturated fatty acid or oil;
   d. a fat soluble vitamin;
   e. a sulfur compound;
   f. a mineral;
   g. an antioxidant;
   h. an amino acid;
   i. an energy stimulator;
   j. steroidal or glycoprotein hormones; and/or
   k. other healing agents selected from glycyrrhizic acid, ribonucleic acids, aloe vera, allantoin, bioperine, berberine hydrochloride, colostrum, dexpanthenol, glucosamine salts, inisitol, phytantriol, pyrrolidine carboxylic acid, jojoba oil, symphytum officinal, polysorbate 80, and vanilla extract.
20. A method of treating skin or tissue comprising applying to the surface of animal skin or tissue an effective amount of a composition comprising the residue of:

a. one or more quaternary ammonium compounds;
b. one or more surfactants;
c. one or more fatty esters;
d. one or more fatty alcohols; and
e. optionally one or more highly polar compounds;
f. wherein the ratio of the sum of the moles of quaternary ammonium compounds, surfactants, and highly polar compounds to the sum of the moles of fatty esters and alcohols is from about 0.8 to about 1.2.

21. The method of claim 20 wherein the ratio is about 1.0.

22. A method of treating skin or tissue comprising applying to the surface of animal skin or tissue an effective amount of an emulsion composition comprising the residue of a fatty phase, wherein:

a. the fatty phase comprises fatty acids, glycerides, and optionally other fatty components, and
b. The molar ratio of fatty acids to glycerides and other fatty components is from about 0.5 to about 3.5.

23. The method of claim 22 wherein the ratio is about 2.0.

24. The method of claim 1 wherein the adduct is an anionic surfactant.

25. The method of claim 1 wherein the fatty acid is mixed with the nitrogenous organic base at a temperature between about 57° C. and about 80° C.

26. The method of claim 1 wherein the fatty acid is an unsaturated or polyunsaturated fatty acid.

* * * * *

UNITED STATES PATENT AND TRADEMARK OFFICE
CERTIFICATE OF CORRECTION

PATENT NO.   : 6,645,510 B1
DATED        : November 11, 2003
INVENTOR(S)  : Coury et al.

It is certified that error appears in the above-identified patent and that said Letters Patent is hereby corrected as shown below:

<u>Column 26,</u>
Line 45, please delete the number "5.0" and substitute the following: -- 3.0 --

Signed and Sealed this

Twenty-seventh Day of April, 2004

JON W. DUDAS
*Acting Director of the United States Patent and Trademark Office*